(12) United States Patent
Kim et al.

(10) Patent No.: US 11,067,554 B2
(45) Date of Patent: Jul. 20, 2021

(54) GAS SENSOR PACKAGE AND SENSING APPARATUS INCLUDING THE SAME

(71) Applicant: Samsung Electronics Co., Ltd., Suwon-si (KR)

(72) Inventors: Minjin Kim, Seoul (KR); Youngdoo Jung, Suwon-si (KR); Eunhee Jung, Hwaseong-si (KR); Sungeun Jo, Incheon (KR); Inho Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 366 days.

(21) Appl. No.: 16/124,385

(22) Filed: Sep. 7, 2018

(65) Prior Publication Data
US 2019/0212312 A1 Jul. 11, 2019

(30) Foreign Application Priority Data

Jan. 10, 2018 (KR) .................. 10-2018-0003171

(51) Int. Cl.
*G01N 33/00* (2006.01)
*G01N 27/12* (2006.01)
(Continued)

(52) U.S. Cl.
CPC ....... *G01N 33/0027* (2013.01); *G01N 27/048* (2013.01); *G01N 27/123* (2013.01);
(Continued)

(58) Field of Classification Search
CPC ............. G01N 33/0027; G01N 27/128; G01N 27/123; G01N 27/407; G01N 27/048;
(Continued)

(56) References Cited

U.S. PATENT DOCUMENTS 5,206,615 A * 4/1993 Fujita .................. G01N 7/10
338/35
7,440,256 B2 10/2008 Hongo et al.
(Continued)

FOREIGN PATENT DOCUMENTS

CN     106298704 A   1/2017
EP        2182497 A1   5/2010
(Continued)

OTHER PUBLICATIONS

Examination report dated Jul. 25, 2019 from the Singapore Patent Office for corresponding Singapore Patent Application, dated Jul. 25, 2019.
(Continued)

*Primary Examiner* — Herbert K Roberts
*Assistant Examiner* — John M Royston
(74) *Attorney, Agent, or Firm* — Muir Patent Law, PLLC (57) ABSTRACT

A gas sensor package includes a package substrate having a hole, the hole having an end that is opened at a first surface of the package substrate; a gas sensor disposed in the hole of the package substrate; a fixing plate disposed on the first surface of the package substrate, the fixing plate having a vent hole extending between a top surface and a bottom surface of the fixing plate, the bottom surface of the fixing plate facing toward the package substrate and the top surface of the fixing plate facing away from the package substrate, and the fixing plate overlapping the hole of the package substrate when viewed in a plan view; and a protective film attached to the fixing plate. The protective film overlaps the vent hole when viewed in a plan view.

20 Claims, 9 Drawing Sheets

(51) Int. Cl.
*G01N 27/407* (2006.01)
*G01N 27/04* (2006.01)
*H01L 23/31* (2006.01)
*H05K 1/03* (2006.01)
*H01L 23/00* (2006.01)
*H01L 23/498* (2006.01)
*H01L 27/02* (2006.01)
*H01L 23/02* (2006.01)

(52) U.S. Cl.
CPC ......... *G01N 27/128* (2013.01); *G01N 27/407* (2013.01); *H01L 23/02* (2013.01); *H01L 23/3107* (2013.01); *H01L 23/49805* (2013.01); *H01L 24/48* (2013.01); *H01L 27/0248* (2013.01); *H05K 1/0306* (2013.01); *H01L 2224/48145* (2013.01); *H01L 2224/48227* (2013.01); *H01L 2924/00014* (2013.01); *H05K 2201/10151* (2013.01)

(58) Field of Classification Search
CPC .. G01N 27/122; G01N 27/12; H01L 27/0248; H01L 23/02; H01L 23/3107; H01L 24/48; H01L 23/49805; H01L 2224/48145; H01L 2924/00014; H01L 2224/48227; H05K 1/0306; H05K 2201/10151
See application file for complete search history.

(56) References Cited

U.S. PATENT DOCUMENTS

| | | | |
|---|---|---|---|
| 8,333,874 B2 * | 12/2012 | Currie | A61B 5/145 204/403.01 |
| 9,232,647 B2 | 1/2016 | Gottwald | |
| 9,506,885 B2 | 11/2016 | Mayer et al. | |
| 9,618,490 B2 | 4/2017 | Paik et al. | |
| 9,629,248 B2 | 4/2017 | Kwon et al. | |
| 2003/0214026 A1 | 11/2003 | Tokuhara | |
| 2008/0061424 A1 | 3/2008 | Murayama et al. | |
| 2008/0102410 A1 | 5/2008 | Kim et al. | |
| 2010/0133629 A1 | 6/2010 | Zhang et al. | |
| 2011/0124113 A1 * | 5/2011 | Azad | G01N 33/5438 436/139 |
| 2014/0311905 A1 * | 10/2014 | Stetter | B01J 31/06 204/424 |
| 2015/0226688 A1 | 8/2015 | Watanabe et al. | |
| 2015/0285772 A1 | 10/2015 | Park et al. | |
| 2015/0287659 A1 | 10/2015 | Liu | |
| 2015/0323510 A1 | 11/2015 | Huynh et al. | |
| 2016/0130136 A1 | 5/2016 | Singh et al. | |
| 2016/0209344 A1 | 7/2016 | Lee | |
| 2017/0250118 A1 | 8/2017 | Yotsuya | |

FOREIGN PATENT DOCUMENTS

| | | |
|---|---|---|
| JP | 64-6833 A | 1/1989 |
| JP | 2015-200644 A | 11/2015 |
| JP | 2016070670 A | 5/2016 |
| JP | 2017-122616 A | 7/2017 |
| KR | 10-2006-0044222 A | 5/2006 |
| KR | 10-1078187 B1 | 11/2011 |
| KR | 10-2015-0089749 A | 8/2015 |
| KR | 10-2015-0092625 A | 8/2015 |
| KR | 10-2015-0092840 A | 8/2015 |
| KR | 10-2016-0122439 A | 10/2016 |
| KR | 10-1709468 B1 | 3/2017 |
| KR | 10-2017-0085395 A | 7/2017 |
| WO | 2016015028 A1 | 1/2016 |

OTHER PUBLICATIONS

Examination report dated Jul. 29, 2019 from the European Patent Office for corresponding European Patent Application, dated Jul. 29, 2019.
Examination report dated Aug. 14, 2020 from the European Patent Office for corresponding European Patent Application.

* cited by examiner

GAS SENSOR PACKAGE AND SENSING APPARATUS INCLUDING THE SAME

CROSS-REFERENCE TO RELATED APPLICATION

This U.S. non-provisional patent application claims priority under 35 U.S.C. § 119 to Korean Patent Application No. 10-2018-0003171, filed on Jan. 10, 2018, in the Korean Intellectual Property Office, the disclosure of which is hereby incorporated by reference in its entirety.

BACKGROUND

Exemplary embodiments of the inventive concepts relate to a gas sensor package and a sensing apparatus including the same.

Generally, a gas sensor may measure the amount of a target gas by using a change in electrical conductivity or electrical resistance due to the adsorption of gas molecules. The gas sensor may be manufactured using a metal oxide semiconductor, a solid electrolyte material, or other organic material.

Air quality generally plays an important role in influencing the health of the human body. As indoor space becomes narrower or more airtight and the amount of chemicals used as building materials increases, air pollution may increase to level which may affect human health. Accordingly, high-precision and high-performance gas sensors may be desired to achieve improved accuracy. Meanwhile, methods of applying a gas sensor to a portable phone or a wearable device are being studied.

SUMMARY

Embodiments of the inventive concepts may provide a gas sensor package capable of improving sensing accuracy and a sensing apparatus including the same.

In an aspect, a gas sensor package may include a package substrate having a hole, the hole having an end that is opened at a first surface of the package substrate; a gas sensor disposed in the hole of the package substrate; a fixing plate disposed on the first surface of the package substrate, the fixing plate having a vent hole extending between a top surface and a bottom surface of the fixing plate, the bottom surface of the fixing plate facing toward the package substrate and the top surface of the fixing plate facing away from the package substrate, and the fixing plate overlapping the hole of the package substrate when viewed in a plan view; and a protective film attached to the fixing plate. The protective film may overlap the vent hole when viewed in a plan view.

In an aspect, a sensing apparatus may include a module board having a first hole extending between a top surface and a bottom surface of the module board; and a gas sensor package mounted on the module board and overlapping the first hole when viewed in a plan view, wherein the gas sensor package comprises: a package substrate having a second hole, the second hole having an end that is opened at a first surface of the package substrate; a gas sensor disposed in the second hole of the package substrate; a fixing plate disposed on the first surface of the package substrate, the fixing plate having a vent hole extending between a top surface and a bottom surface of the fixing plate, the bottom surface of the fixing plate facing toward the package substrate and the top surface of the fixing plate facing away from the package substrate, the fixing plate overlapping the second hole of the package substrate when viewed in a plan view; and a protective film attached to the fixing plate. The fixing plate may overlap the hole when viewed in a plan view. The first surface of the package substrate may face the module board.

BRIEF DESCRIPTION OF THE DRAWINGS

The inventive concepts according to exemplary embodiments will become more apparent in view of the attached drawings and accompanying detailed description.

DETAILED DESCRIPTION OF THE EMBODIMENTS

Hereinafter, exemplary embodiments of the inventive concepts will be described in detail with reference to the accompanying drawings. The same reference numerals or the same reference designators may denote the same elements or components throughout the specification.

A gas sensor package and a sensing apparatus including the same, according to exemplary embodiments of the inventive concepts, will be described hereinafter.

Figure 1A:
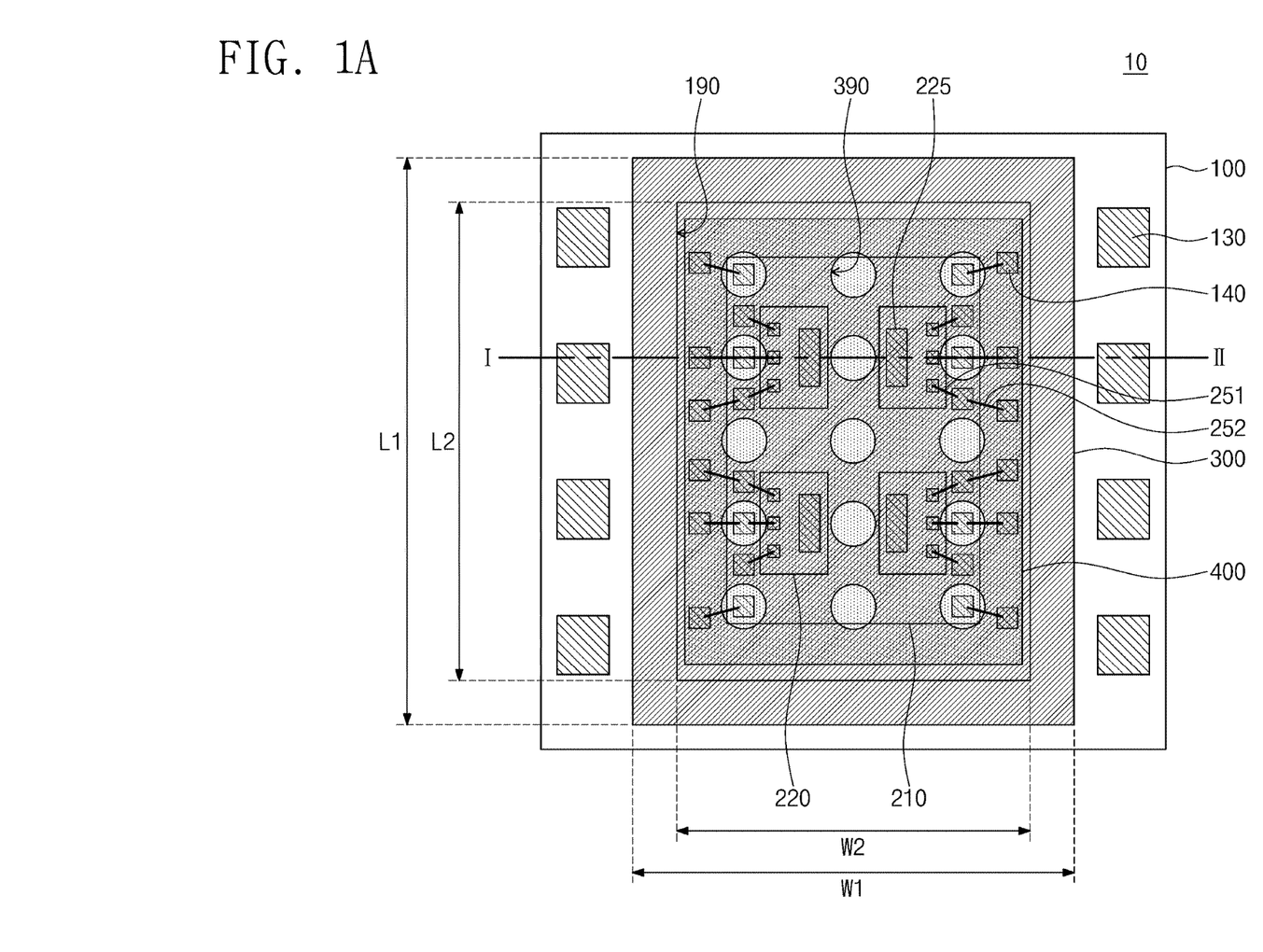
FIG. 1A is a plan view illustrating a gas sensor package according to some exemplary embodiments of the inventive concepts.
Figure 1B:
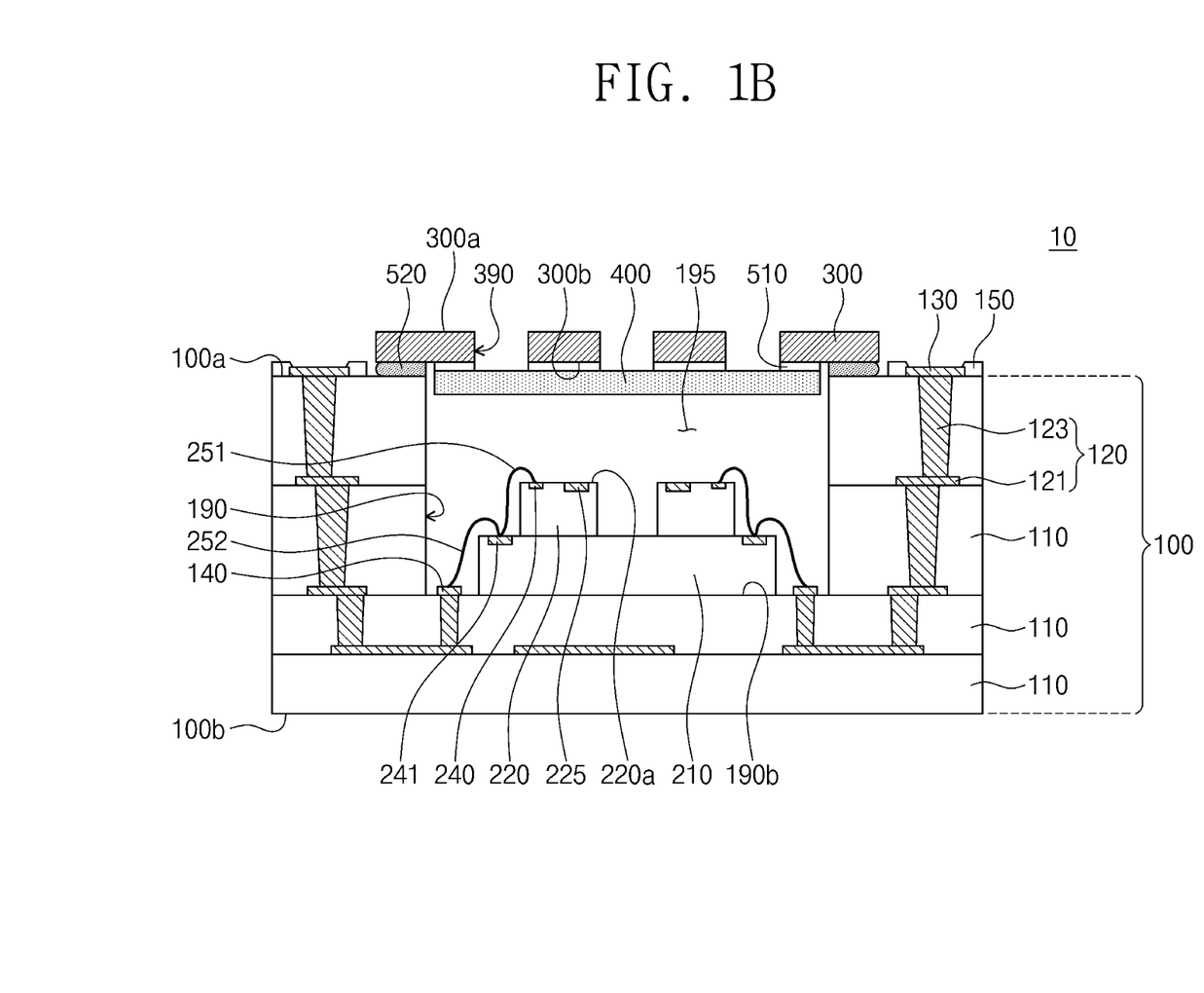
FIG. 1B is a cross-sectional view taken along a line I-II of FIG. 1A.

FIG. 1A is a plan view illustrating a gas sensor package according to some embodiments of the inventive concepts. FIG. 1B is a cross-sectional view taken along a line I-II of FIG. 1A.

Referring to FIGS. 1A and 1B, a gas sensor package 10 may include a package substrate 100, a control device 210 (e.g., control circuitry), a sensing device 220 (e.g., a semiconductor integrated circuit chip forming a sensor), a fixing plate 300, and a protective film 400. The fixing plate 300 may be a plate-like member having uniform thickness throughout the body thereof.

The package substrate 100 may have a hole 190. The package substrate 100 may have a first surface 100a and a second surface 100b which are opposite to each other. The first surface 100a may also be referred to as the top surface of the package substrate 100 and the second surface 100b may also be referred to as the bottom surface of the package substrate 100. The hole 190 may have an end that is opened at the first surface 100a of the package substrate 100. The hole 190 may extend from the first surface 100a of the package substrate 100 toward the second surface 100b of the package substrate 100. In an exemplary embodiment, the hole 190 may be formed by removing a portion of the package substrate 100. The hole 190 may penetrate a portion of the package substrate 100. A bottom surface 190b of the hole 190 may be provided in the package substrate 100. The bottom surface 190b of the hole 190 may be spaced apart from the second surface 100b of the package substrate 100. As illustrated in FIG. 1A, the hole 190 may be formed in a central portion of the package substrate 100 when viewed in a plan view. Since the package substrate 100 has the hole 190, a cavity 195 may be provided. For example, the cavity 195 may correspond to at least a portion of an inner space of the hole 190. The cavity 195 may be defined by the package substrate 100 and the protective film 400. For example, the cavity 195 may be a space surrounded by the package substrate 100 and the protective film 400. The cavity 195 may be occupied by a gas. The gas may include an analysis target material composition.

The package substrate 100 may include a base layer 110 and a conductive structure 120. For example, a printed circuit board (PCB) may be used as the package substrate 100. The base layer 110 may include a non-conductive material composition. For example, the base layer 110 may include ceramic, a carbon-containing material composition (e.g., graphite or graphene), and/or polymer. The base layer 110 may include a plurality of base layers 110 sequentially stacked. Alternatively, the package substrate 100 may have a single base layer 110. The conductive structure 120 may include a conductive pattern 121 and a conductive via 123. The conductive pattern 121 may be provided between the base layers 110 or on an uppermost one of the base layers 110. The conductive via 123 may penetrate at least one of the base layers 110 and may be electrically connected to the conductive pattern 121. In the present specification, it is understood that when an element is referred to as being "electrically connected" to another element, it may be connected directly to the other element or intervening elements may be present. As used herein, and unless indicated otherwise, items described as being "electrically connected" are configured such that an electrical signal can be passed from one item to the other.

The conductive pattern 121 and the conductive via 123 may include a metal such as copper or aluminum. In some embodiments, the conductive structure 120 may further be provided between the second surface 100b of the package substrate 100 and the bottom surface 190b of the hole 190. Thus, paths of electrical signals in the package substrate 100 may be various according to desired design specifications. A passivation layer 150 may be provided on the first surface 100a of the package substrate 100. The passivation layer 150 may include a solder-resist material composition.

An external connection pad 130 may be disposed on the first surface 100a of the package substrate 100. The external connection pad 130 may be exposed by the passivation layer 150. The external connection pad 130 may be electrically connected to the conductive structure 120. The conductive structure 120 may be electrically connected to an external device or apparatus external to the gas sensor package 10 through the external connection pad 130. The external connection pad 130 may include a metal such as copper or aluminum. In some embodiments, the external connection pad 130 may be provided in plurality. Even though not shown in the drawings, a solder may be provided on the external connection pad 130.

Bonding pads 140 may be provided on the bottom surface 190b of the hole 190. The bonding pads 140 may be electrically connected to the conductive structure 120. Planar arrangement of the bonding pads 140 is not limited to illustration of FIG. 1A but may be variously changed. According to exemplary embodiments, a surface area of each of the bonding pads 140 may be smaller than a surface area of each of the conductive pattern 121. For example, the length of each of the bonding pads 140 in a direction parallel to the bottom surface 190b of the hole 190 may be smaller than the length of each of the conductive pattern 121 in the direction parallel to the bottom surface 190b of the hole 190.

The various pads of a device described herein may be conductive terminals connected to internal wiring of the device, and may transmit signals and/or supply voltages between an internal wiring and/or internal circuit of the device and an external source. For example, chip pads of a semiconductor chip may electrically connect to and transmit supply voltages and/or signals between an integrated circuit of the semiconductor chip and a device to which the semiconductor chip is connected. The various pads may be provided on or near an external surface of the device and may generally have a planar surface area (often larger than a corresponding surface area of the internal wiring to which they are connected) to promote connection to a further terminal, such as a bump or solder ball, and/or an external wiring.

The devices 210 and 220 may be disposed on the bottom surface 190b of the hole 190. The devices 210 and 220 may be spaced apart from sidewalls of the hole 190. As described above, the devices 210 and 220 may include the control device 210 and the sensing device 220.

Those skilled in the art will appreciate that the control device 210 and the sensing device 220 may be physically implemented by electronic circuits such as logic circuits, discrete components, microprocessors, hard-wired circuits, wiring connections, and the like, which may be formed using semiconductor-based fabrication techniques or other manufacturing technologies.

According to exemplary embodiments, the control device 210 may include a semiconductor chip. The control device 210 may include integrated circuits including complementary metal-oxide semiconductor (CMOS) transistors therein. The control device 210 may control the sensing device 220. The control device 210 may be referred to as a controller.

The sensing device 220 may be disposed on a top surface of the control device 210. The sensing device 220 may be a gas sensor chip to sense a gas. The sensing device 220 may include a plurality of sensing devices 220 spaced apart from each other in a horizontal direction (a direction parallel to the bottom surface 190b of the hole 190) on the top surface of the control device 210. Top surfaces 220a of the sensing devices 220 may function as sensing surfaces. In some embodiments, the sensing devices 220 may include sensing electrodes (not shown) which are provided on the top surfaces 220a of the sensing devices 220 or are provided adjacent to the top surfaces 220a. Each of the sensing devices 220 may include a sensing portion 225 and chip pads 240, which are disposed on the top surface 220a thereof. The sensing portion 225 and the chip pad 240 of each sensing device 220 may be disposed on the top surface 220a of the sensing device 220 spaced apart from each other by a predetermined distance in a direction parallel to parallel to the bottom surface 190b of the hole 190. For example, the sensing portion 225 and the chip pad 240 may be disposed on opposing edges of the top surface 220a of the sensing device 220. The sensing portion 225 may include a sensing pad to which an analysis target gas is adsorbed. The sensing device 220 may be provided in plural and may be stacked on the top surface of the control device 210 spaced apart from each other by a predetermined distance in a direction parallel to the bottom surface 190b of the hole 190. For example, one of the plurality of sensing devices 220 may be disposed on one edge of the top surface of the control device 210 and the other one of the plurality of sensing devices 220 may be disposed on the other edge of the top surface of the control device 210 in a direction parallel to the bottom surface 190b of the hole 190.

According to exemplary embodiments, a type of a gas adsorbed on the sensing portion 225 may be determined depending on a type of a material composition of the sensing portion 225. A material composition of the sensing portion 225 of one of the sensing devices 220 may be different from a material composition of the sensing portion 225 of another of the sensing devices 220. Here, the material composition of the sensing portion 225 may mean a material composition of a sensing pad included in the sensing portion 225. A type of a gas adsorbed on the sensing portion 225 of the one sensing device 220 may be different from a type of a gas adsorbed on the sensing portion 225 of the other sensing device 220. Thus, the sensing devices 220 may sense different types of gases. As a result, the gas sensor package 10 may quantitatively or qualitatively analyze various types of gases. The sensing devices 220 may be electrically connected to the control device 210 through first bonding wires 251. For example, the first bonding wires 251 may electrically connect the chip pads 240 of the sensing devices 220 to chip pads 241 of the control device 210. The control device 210 may be electrically connected to the bonding pads 140 through second bonding wires 252. For example, the second bonding wires 252 may electrically connect the chip pads 241 of the control device 210 to the bonding pads 140. Thus, the control device 210 may be electrically connected to the conductive structure 120 of the package substrate 100. In addition, the sensing devices 220 may be electrically connected to the package substrate 100 through the control device 210. In certain embodiments, at least one of the control device 210 and the sensing devices 220 may be electrically connected to the package substrate 100 by a flip-chip bonding method. In the present specification, it is understood that when an element or component is electrically connected to the package substrate 100, it may be electrically connected to the conductive structure 120 of the package substrate 100. In addition, it is understood that when an element or component is electrically connected to the control device 210 or sensing device 220, it may be electrically connected to integrated circuits of the control device 210 or sensing device 220. Unlike FIG. 1B, at least one of the sensing devices 220 may be disposed on the bottom surface 190b of the hole 190 and may be laterally spaced apart from the control device 210.

The fixing plate 300 may be disposed on the first surface 100a of the package substrate 100. A width W1 of the fixing plate 300 may be greater than a width W2 of the hole 190, as illustrated in FIG. 1A. A length L1 of the fixing plate 300 may be greater than a length L2 of the hole 190, as illustrated in FIG. 1A. The fixing plate 300 may include a conductive material composition such as a metal. Alternatively, the fixing plate 300 may include a non-conductive material composition such as polymer or silicon. The fixing plate 300 may have at least one vent hole 390. As illustrated in FIG. 1A, the vent hole 390 of the fixing plate 300 may overlap the hole 190 of the package substrate 100 when viewed in a plan view. The fixing plate 300 may include a top surface 300a and a bottom surface 300b opposite to the top surface 300a of the fixing plate 300. The bottom surface 300b of the fixing plate 300 may face toward the package substrate 100 and the top surface 300a of the fixing plate 300 may face away from the package substrate 100. The vent hole 390 may penetrate the top surface 300a and the bottom surface 300b of the fixing plate 300. For example, the hole 390 may extend between the top surface 300a and the bottom surface 300b of the fixing plate 300. The vent hole 390 of the fixing plate 300 may be connected to an external system external to the gas sensor package 10. External material compositions may be provided into the vent hole 390 of the fixing plate 300. The external material compositions may include a gas and impurities. The impurities may include moisture and/or dust.

The protective film 400 may be provided on the fixing plate 300. In some embodiments, the protective film 400 may be adhered to (e.g., attached to) the bottom surface 300b of the fixing plate 300. The protective film 400 may overlap the vent hole 390 of the fixing plate 300 when viewed in a plan view. The external gas may pass through the protective film 400 and may then be provided into the hole 190 (e.g., the cavity 195) of the package substrate 100. The external gas may include the analysis target material composition. In some embodiments, the external gas may pass through the protective film 400 through pores (not shown) of the protective film 400. The sensing devices 220 may sense or measure the gas provided in the cavity 195. The external impurities may be difficult to pass through the pores of the protective film 400. Material compositions passing through the protective film 400 may be controlled by controlling a type of a material composition of the protective film 400. According to exemplary embodiments, the protective film 400 may include a hydrophobic material composition to prevent hydrophilic impurities (e.g., moisture) from flowing into the hole 190 (i.e., the cavity 195). The hydrophobic material composition may include, for example, poly(tetrafluoroethylene) (PTFE). The protective film 400 may include a waterproof film. The top surfaces 220a of the sensing devices 220 may face the protective film 400. The protective film 400 may be homogenously formed of the same material.

The phrase "passing through the protective film 400" may include "passing through pores (not shown) of the waterproof film of the protective film 400." When the pores of the waterproof film of the protective film 400 have a diameter less than about 0.1 µm, the gas may have difficulty in passing through the protective film 400. When the pores of the waterproof film of the protective film 400 have a diameter greater than about 10 µm, the impurities may pass through the protective film 400. In some embodiments, the pores of the waterproof film of the protective film 400 may have a diameter ranging from about 0.1 µm to about 10 µm. The protective film 400 may accordingly allow the gas to pass through, but not allow the impurities to pass through. A thickness of the waterproof film of the protective film 400 may be appropriately adjusted to select gas passing through the protective film 400. In some embodiments, the thickness of the waterproof film of the protective film 400 may fall within a range from about 10 µm to about 500 µm. The protective film 400 may thus selectively allow the gas to pass through.

According to some embodiments of the inventive concepts, the external impurities may be blocked by the protective film 400, and thus it is possible to prevent sensing noise from being generated by impurities. As a result, the accuracy of the sensing devices 220 may be improved. In addition, damage of the sensing devices 220 by the impurities may be reduced or prevented. The fixing plate 300 may prevent the protective film 400 from being damaged by external stress. The external stress may be, for example, a physical impact.

The protective film 400 may be flexible or relatively soft. The protective film 400 may be firmly fixed to the fixing plate 300. An adhesive film 510 may be provided between the fixing plate 300 and the protective film 400. The adhesive film 510 may include a polymer. The protective film 400 may be adhered to the fixing plate 300 through the adhesive film 510. The adhesive film 510 may seal a gap between the protective film 400 and the fixing plate 300. Due to the adhesive film 510, the external impurities may be difficult to flow into the hole 190 (i.e., the cavity 195). The adhesive film 510 may not extend into the vent hole 390. For example, bottom surface of the adhesive film 510 may contact top surface of the protective film 400 and the bottom surface 300*b* of the fixing plate 300 may contact top surface of the adhesive film 510.

An adhesive portion 520 may be provided between the package substrate 100 and the fixing plate 300. The fixing plate 300 may be adhered to the package substrate 100 through the adhesive portion 520. The adhesive portion 520 may include a resin. The adhesive portion 520 may seal a gap between the package substrate 100 and the fixing plate 300. Thus, the external impurities may be more difficult to flow into the hole 190 (i.e., the cavity 195). The fixing plate 300, together with the top surface of the second surface 100*b* of the package substrate 100, opposing side surfaces of the first surface 100*a* of the package substrate 100, the protective film 400, adhesive portion 520 and the adhesive film 510, may encapsulate the control device 210 and sensing devices 220 and seal the same within cavity 195. With the exception of gas allowed to pass through the protective film 400, the cavity 195 may be hermetically sealed and thus only allow gas to flow in an out of cavity 195 via pores of the protective film 400.

Figure 1C:
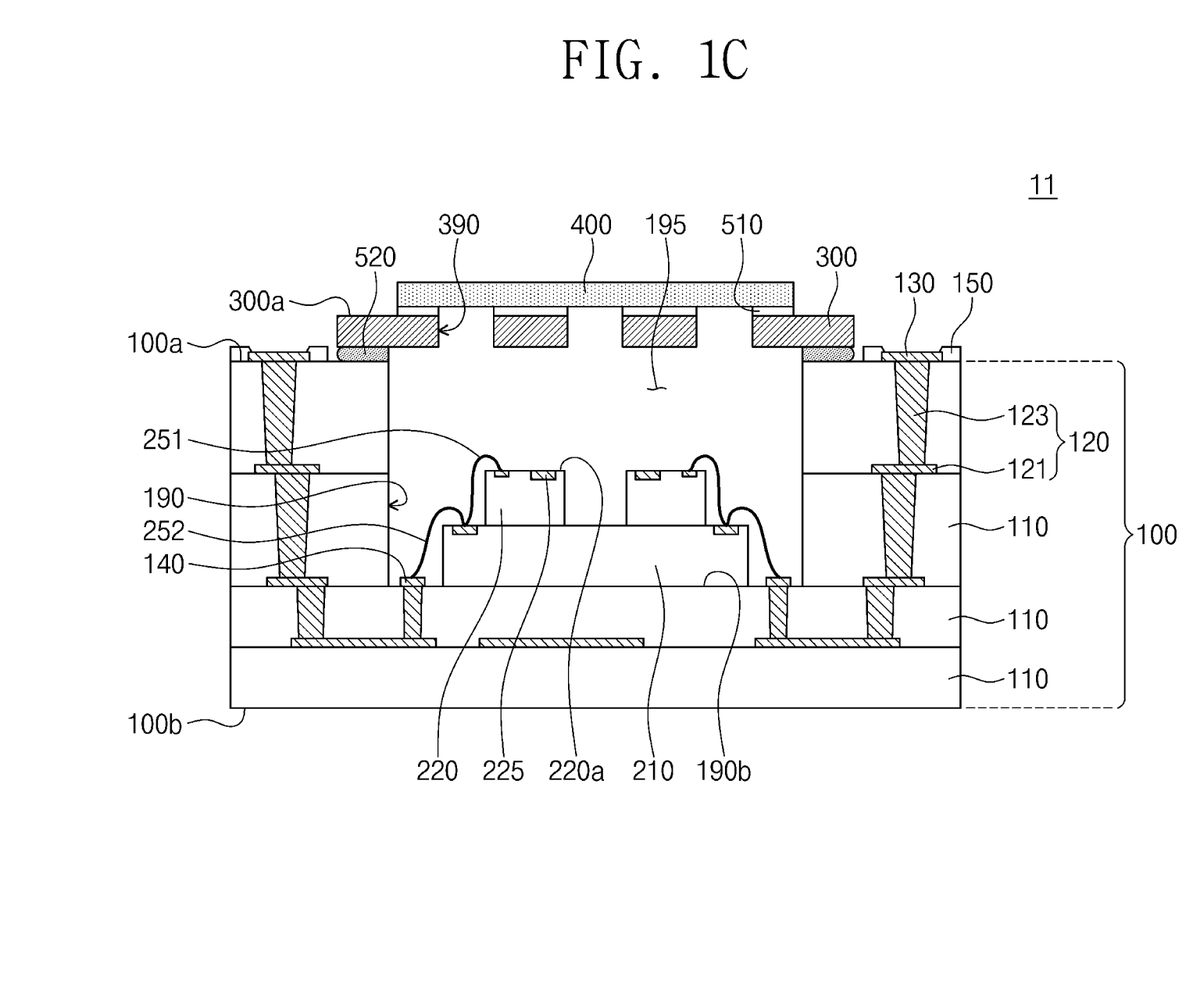
FIG. 1C is a cross-sectional view illustrating a gas sensor package according to some exemplary embodiments of the inventive concepts.

FIG. 1C is a cross-sectional view corresponding to the line I-II of FIG. 1A to illustrate a gas sensor package according to some embodiments of the inventive concepts.

Referring to FIG. 1C, a gas sensor package 11 may include a package substrate 100, a control device 210, a sensing device 220, a fixing plate 300, and a protective film 400. The package substrate 100, the control device 210, the sensing device 220, the fixing plate 300 and the protective film 400 may be substantially the same as described above with reference to FIGS. 1A and 1B. However, the protective film 400 may be adhered to the top surface 300*a* of the fixing plate 300. The adhesive film 510 may be provided between the top surface 300*a* of the fixing plate 300 and the protective film 400. For example, bottom surface of the adhesive film 510 may contact top surface 300*a* of the fixing plate 300 and bottom surface of the protective film 400 may contact top surface of the adhesive film 510.

Figure 2A:
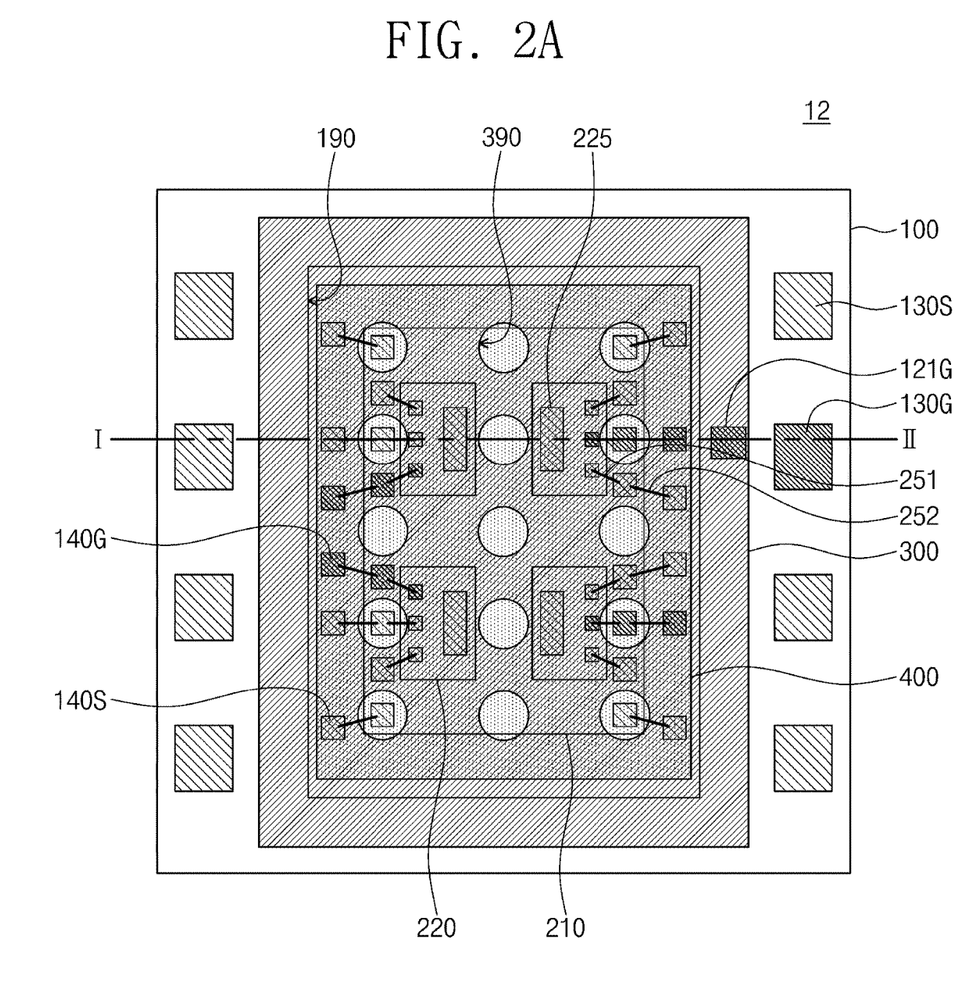
FIG. 2A is a plan view illustrating a gas sensor package according to some exemplary embodiments of the inventive concepts.
Figure 2B:
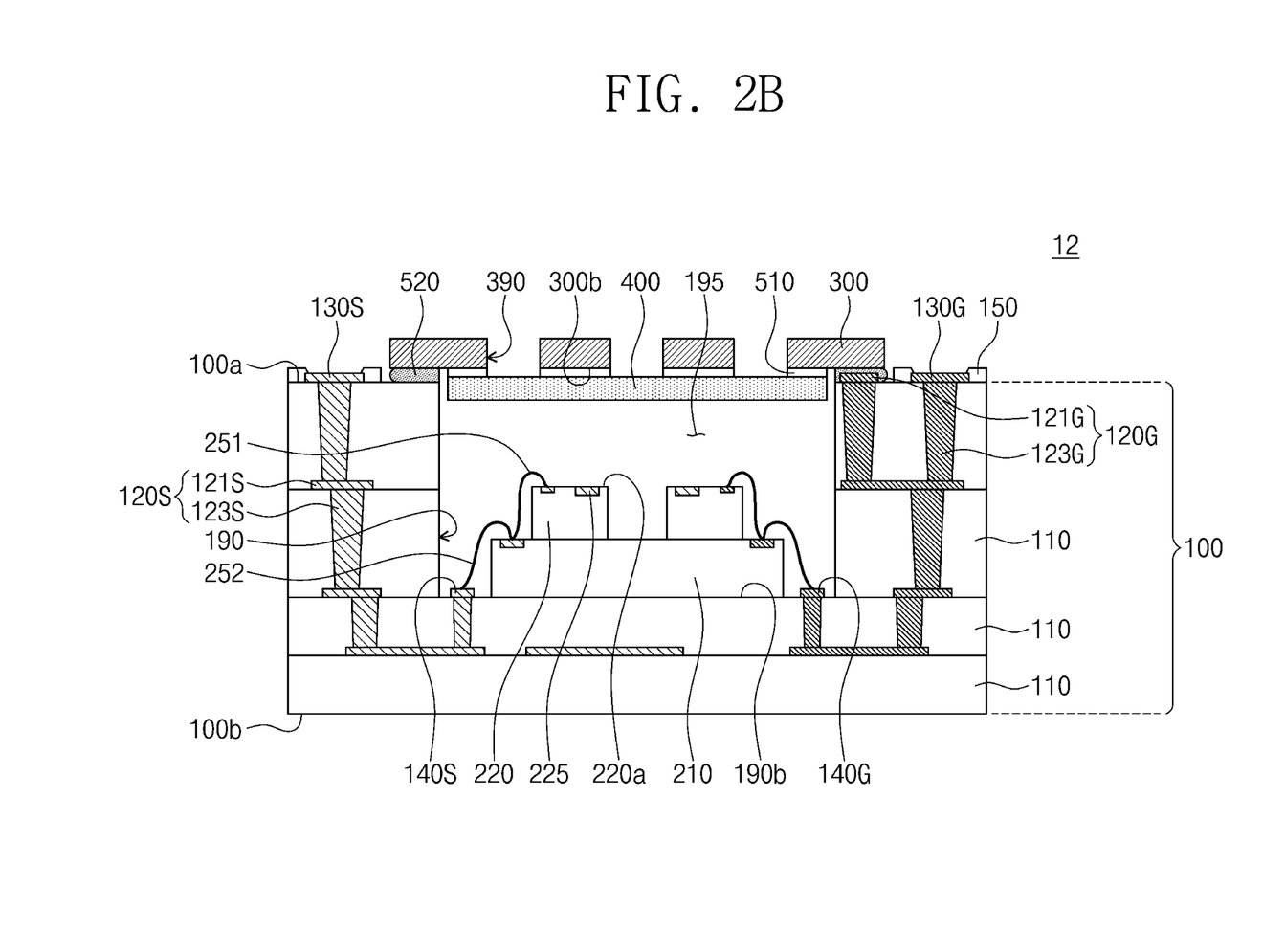
FIG. 2B is a cross-sectional view taken along a line I-II of FIG. 2A.

FIG. 2A is a plan view illustrating a gas sensor package according to some exemplary embodiments of the inventive concepts. FIG. 2B is a cross-sectional view taken along a line I-II of FIG. 2A.

Referring to FIGS. 2A and 2B, a gas sensor package 12 may include a package substrate 100, a control device 210, a sensing device 220, a fixing plate 300, and a protective film 400. The control device 210, the sensing device 220, the fixing plate 300 and the protective film 400 may be substantially the same as described above with reference to FIGS. 1A and 1B. The package substrate 100 may include base layers 110 and a plurality of conductive structures 120G and 120S. The conductive structures 120G and 120S may include a signal structure 120S and a ground structure 120G. The signal structure 120S may include a signal pattern 121S and a signal via 123S. The ground structure 120G may be electrically insulated from the signal structure 120S. Positions and arrangement of the signal pattern 121S and the signal via 123S may be substantially the same as those of the conductive pattern 121 and the conductive via 123 of FIGS. 1A and 1B. For example, the signal pattern 121S may be provided between the base layers 110. The signal via 123S may penetrate at least one of the base layers 110 and may be electrically connected to the signal pattern 121S. The ground structure 120G may include a ground pattern 121G and a ground via 123G. Positions and arrangement of the ground pattern 121G and the ground via 123G may be similar to those of the conductive pattern 121 and the conductive via 123 of FIGS. 1A and 1B. The ground pattern 121G may be provided between the base layers 110 or on an uppermost one of the base layers 110. The ground pattern 121G on the uppermost base layer 110 may vertically overlap the fixing plate 300. A portion (e.g., the ground pattern 121G on the uppermost base layer 110) of the ground structure 120G may be exposed on the first surface 100*a* of the package substrate 100. The ground via 123G may penetrate at least one of the base layers 110 and may be electrically connected to the ground pattern 121G. The signal pattern 121S, the signal via 123S, the ground pattern 121G and the ground via 123G may include a metal such as copper or aluminum.

External connection pads 130S and 130G may include a signal pad 130S and a ground pad 130G. The signal pad 130S and the ground pad 130G may be disposed on the first surface 100*a* of the package substrate 100. The signal pad 130S and the ground pad 130G may be electrically connected to the signal structure 120S and the ground structure 120G, respectively. The ground pad 130G may be electrically insulated from the signal pad 130S. In an embodiment, the signal pad 130S may be provided in plurality. The number of the ground pad 130G may be less than the number of the signal pad(s) 130S. A signal solder (not shown) may be provided on the signal pad 130S, and a ground solder (not shown) may be provided on the ground pad 130G.

Bonding pads 140S and 140G may be provided on the bottom surface 190*b* of the hole 190. The bonding pads 140S and 140G may include a signal bonding pad 140S and a ground bonding pad 140G. The signal bonding pad 140S and the ground bonding pad 140G may be electrically connected to the signal structure 120S and the ground structure 120G, respectively. In an embodiment, the signal bonding pad 140S may be provided in plurality. The ground bonding pad 140G may be electrically insulated from the signal bonding pads 140S. The number of the ground bonding pad 140G may be less than the number of the signal bonding pads 140S. The control device 210 may be electrically connected to the signal bonding pads 140S and the ground bonding pad 140G through the second bonding wires 252. For example, at least one of the second bonding wires 252 may be connected to the ground bonding pad 140G. Some of the second bonding wires 252 may be connected to the signal bonding pads 140S, respectively. Thus, the control device 210 may be electrically connected to the signal pads 130S and the ground pad 130G. The chip pads 240 (as shown in FIG. 1B) of the sensing devices 220 may be electrically connected to the chip pads 241 (as shown in FIG. 1B) of the control device 210. The sensing devices 220 may be electrically connected to the signal bonding pads 140S and the ground bonding pad 140G through the control device 210.

Thus, the sensing devices 220 may be electrically connected to the signal pads 130S and the ground pad 130G.

The fixing plate 300 may be disposed on the first surface 100a of the package substrate 100. The fixing plate 300 may include a conductive material such as a metal. The metal may include stainless steel. Since the fixing plate 300 has conductivity, the fixing plate 300 may block electromagnetic interference (EMI) of the gas sensor package 12. The electromagnetic interference (EMI) means that electromagnetic wave irradiated or transmitted from an electronic element causes troubles of signal reception/transmission of another electronic element. The fixing plate 300 may prevent operations of the control and sensing devices 210 and 220 from disturbing operations of another package and/or may prevent operations of another package from disturbing the operations of the control and sensing devices 210 and 220.

The fixing plate 300 may be adhered to the package substrate 100 by an adhesive portion 520. The adhesive portion 520 may include a conductive adhesive. For example, the adhesive portion 520 may include an insulating resin and conductive particles dispersed in the insulating resin. The insulating resin may include an epoxy-based resin, and the conductive particles may include a metal. The adhesive portion 520 may extend between the fixing plate 300 and the ground pattern 121G exposed on the first surface 100a of the package substrate 100. The fixing plate 300 may be electrically connected to the ground structure 120G through the adhesive portion 520. Thus, the fixing plate 300 may be grounded. The adhesive portion 520 may be spaced apart from the signal pads 130S. The fixing plate 300 may be electrically insulated from the signal structure 120S and the signal pad 130S. If the fixing plate 300 formed of the conductive material is not grounded, charges may be stored in the fixing plate 300. If a certain amount of the charges are accumulated in the fixing plate 300, the charges may flow from the fixing plate 300 into other conductive elements or components to damage the other conductive elements or components. Here, the other conductive elements or components may include at least one of the integrated circuits in the control device 210, the integrated circuits in the sensing devices 220, the signal structure 120S, the ground structure 120G, the first bonding wires 251, or the second bonding wires 252. The fixing plate 300 may be electrically connected to the ground pad 130G through the ground structure 120G. As a result, reliability of the gas sensor package 12 may be improved. The passivation layer 150 may not extend between the fixing plate 300 and the ground pattern 121G exposed on the first surface 100a of the package substrate 100.

In certain embodiments, the protective film 400 of FIG. 2B may be disposed on the top surface of the fixing plate 300, as described with reference to FIG. 1C.

Figure 3:
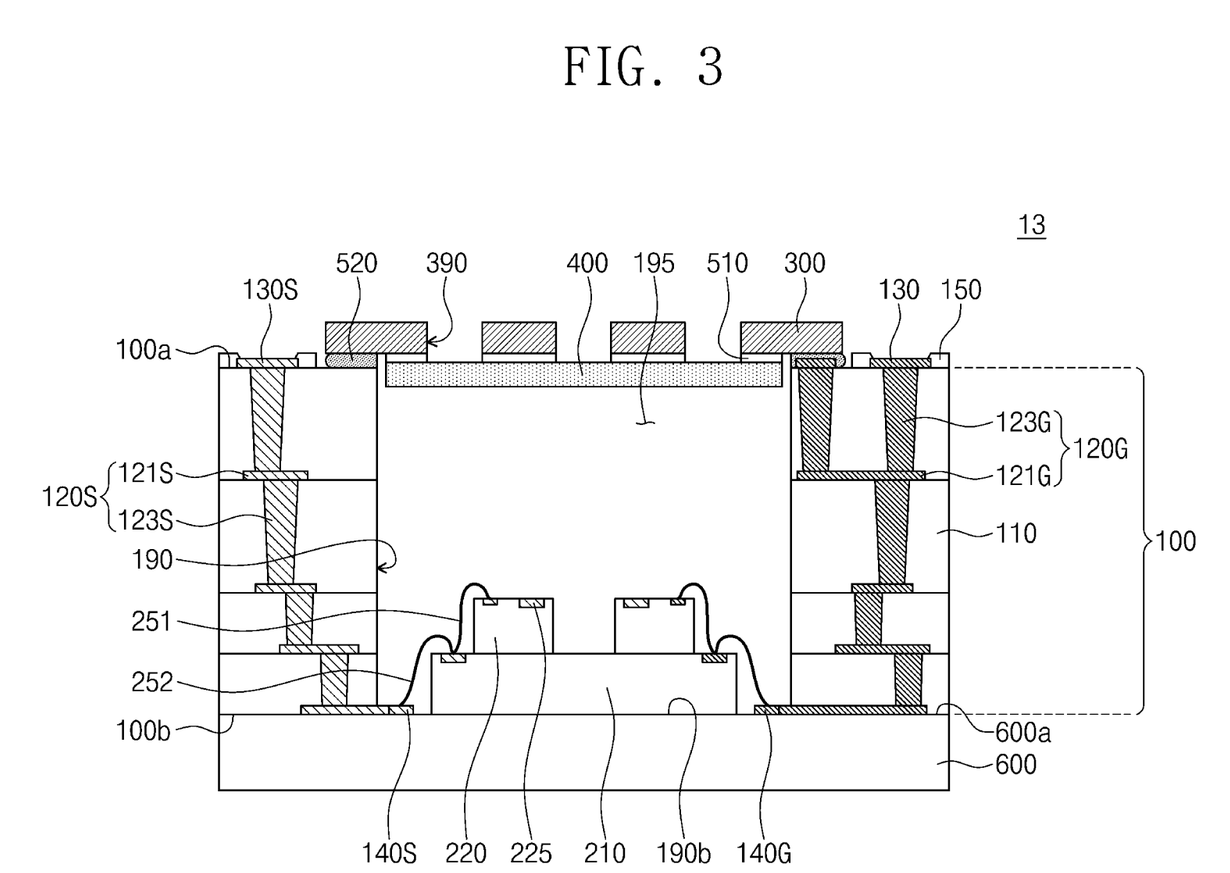
FIG. 3 is a cross-sectional view illustrating a gas sensor package according to some exemplary embodiments of the inventive concepts.

FIG. 3 is a cross-sectional view corresponding to the line I-II of FIG. 1A to illustrate a gas sensor package according to some embodiments of the inventive concepts. Hereinafter, the descriptions to the same elements and technical features as in the above embodiments will be omitted or mentioned briefly for the purpose of ease and convenience in explanation. Hereinafter, a singular signal bonding pad 140S will be described.

Referring to FIG. 3, a gas sensor package 13 may include a package substrate 100, a control device 210, a sensing device 220, a fixing plate 300, a protective film 400, and a support substrate 600. The package substrate 100, the control device 210, the sensing device 220, the fixing plate 300 and the protective film 400 may be substantially the same as described above with reference to FIGS. 1A and 1B, 1C, or 2A and 2B. However, the hole 190 may penetrate the first surface 100a and the second surface 100b of the package substrate 100.

The support substrate 600 may be disposed on the second surface 100b of the package substrate 100. For example, the package substrate 100 may be disposed on a top surface 600a of the support substrate 600. The support substrate 600 may overlap the hole 190 when viewed in a plan view. For example, the support substrate 600 may be a printed circuit board, a metal plate, or a non-conductive plate. A cavity 195 may be defined by the support substrate 600, the package substrate 100, and the protective film 400. For example, the cavity 195 may be a space surrounded by the support substrate 600, the package substrate 100 and the protective film 400. For example, the cavity 195 may correspond to at least a portion of an inner space of the hole 190.

The signal structure 120S and the ground structure 120G may not be electrically connected to the support substrate 600. Alternatively, the signal structure 120S or the ground structure 120G may be electrically connected to conductive elements or components in the support substrate 600. The conductive elements or components of the support substrate 600 may include interconnection lines and/or vias. In this exemplary embodiment, the conductive elements or components of the support substrate 600 may further function as an electrical path of the signal structure 120S or the ground structure 120G.

The control device 210 may be disposed on the top surface 600a of the support substrate 600. The sensing devices 220 may be disposed on the control device 210. A portion of the top surface 600a of the support substrate 600 may correspond to a bottom surface 190b of the hole 190. The control device 210 and the sensing devices 220 may be provided in the hole 190. The signal bonding pad 140S and the ground bonding pad 140G may be disposed on the top surface 600a of the support substrate 600. The control device 210 and the sensing devices 220 may be electrically connected to the signal bonding pad 140S and the ground bonding pad 140G. A signal pattern 121S of the signal structure 120S may extend along the bottom surface 190b of the hole 190 so as to be connected to the signal bonding pad 140S. A ground pattern 121G of the ground structure 120G may extend along the bottom surface 190b of the hole 190 so as to be connected to the ground bonding pad 140G. Alternatively, the signal structure 120S and the ground structure 120G may be electrically connected to the signal bonding pad 140S and the ground bonding pad 140G through the conductive elements or components of the support substrate 600, respectively.

Figure 4:
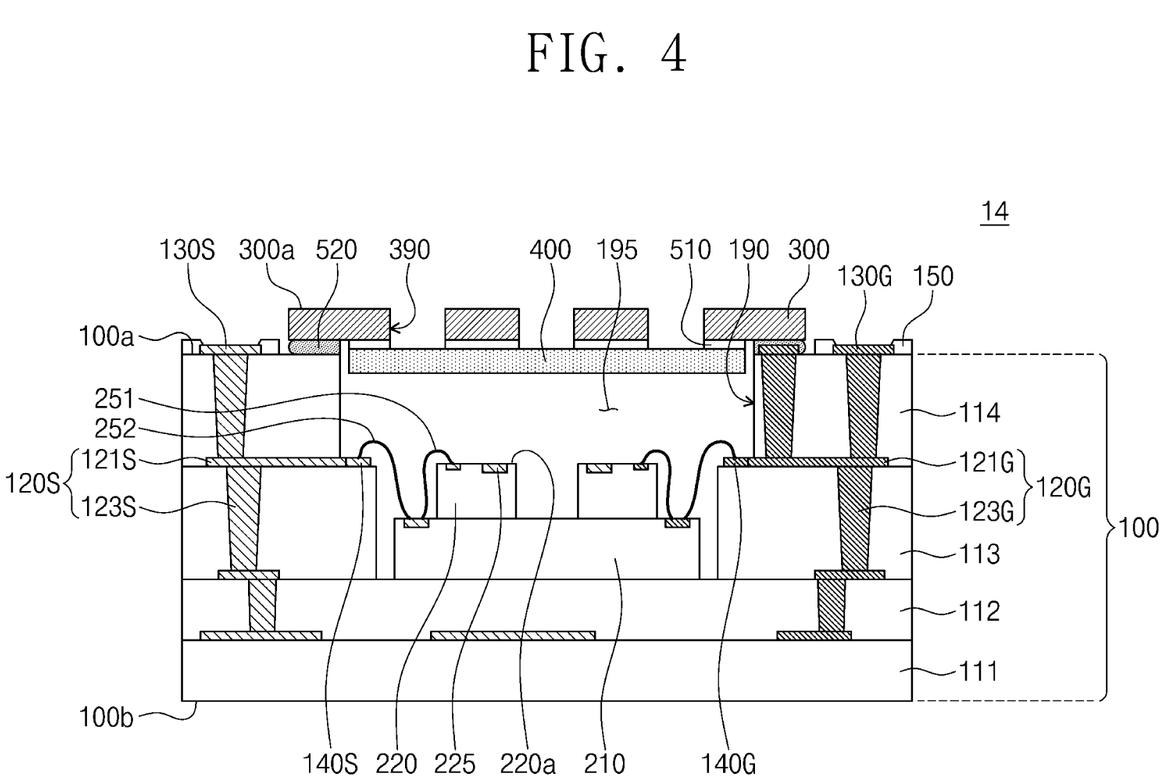
FIG. 4 is a cross-sectional view illustrating a gas sensor package according to some exemplary embodiments of the inventive concepts.

FIG. 4 is a cross-sectional view corresponding to the line I-II of FIG. 1A to illustrate a gas sensor package according to some embodiments of the inventive concepts. Hereinafter, the descriptions to the same elements and technical features as in the above embodiments will be omitted or mentioned briefly for the purpose of ease and convenience in explanation.

Referring to FIG. 4, a gas sensor package 14 may include a package substrate 100, a control device 210, a sensing device 220, a fixing plate 300, and a protective film 400. The control device 210, the sensing device 220, the fixing plate 300 and the protective film 400 may be substantially the same as described above with reference to FIGS. 1A and 1B, 1C, or 2A and 2B. Base layers of the package substrate 100 may include a first lower base layer 111, a second lower base layer 112, a first upper base layer 113, and a second upper base layer 114, which are sequentially stacked. A hole 190 of the package substrate 100 may be provided in the first and second upper base layers 113 and 114. The hole 190 may not be provided in the first and second lower base layers 111 and 112.

The first and second upper base layers 113 and 114 may constitute a stepped structure. A width of the hole 190 in the second upper base layer 114 may be greater than a width of the hole 190 in the first upper base layer 113. The second upper base layer 114 may expose a portion of a top surface of the first upper base layer 113. For example, the portion of the top surface of the first upper base layer 113 may be exposed by the hole 190. A signal bonding pad 140S and a ground bonding pad 140G may be disposed on the exposed top surface of the first upper base layer 113. A signal pattern 121S on the first upper base layer 113 may extend to be connected to the signal bonding pad 140S. A ground pattern 121G on the first upper base layer 113 may extend to be connected to the ground bonding pad 140G. The control device 210 may be electrically connected to the signal bonding pad 140S and the ground bonding pad 140G through the second bonding wires 252. The sensing devices 220 may be electrically connected to the signal bonding pad 140S and the ground bonding pad 140G through the first bonding wires 251, the control device 210, and the second bonding wires 252.

In certain embodiments, the first or second upper base layers 113 or 114 may include a plurality of stacked layers. In certain embodiments, at least one of the first and second lower base layers 111 and 112 may be omitted. In certain embodiments, the fixing plate 300 may not be grounded. In certain embodiments, the protective film 400 may be disposed on the top surface 300a of the fixing plate 300.

Figure 5:
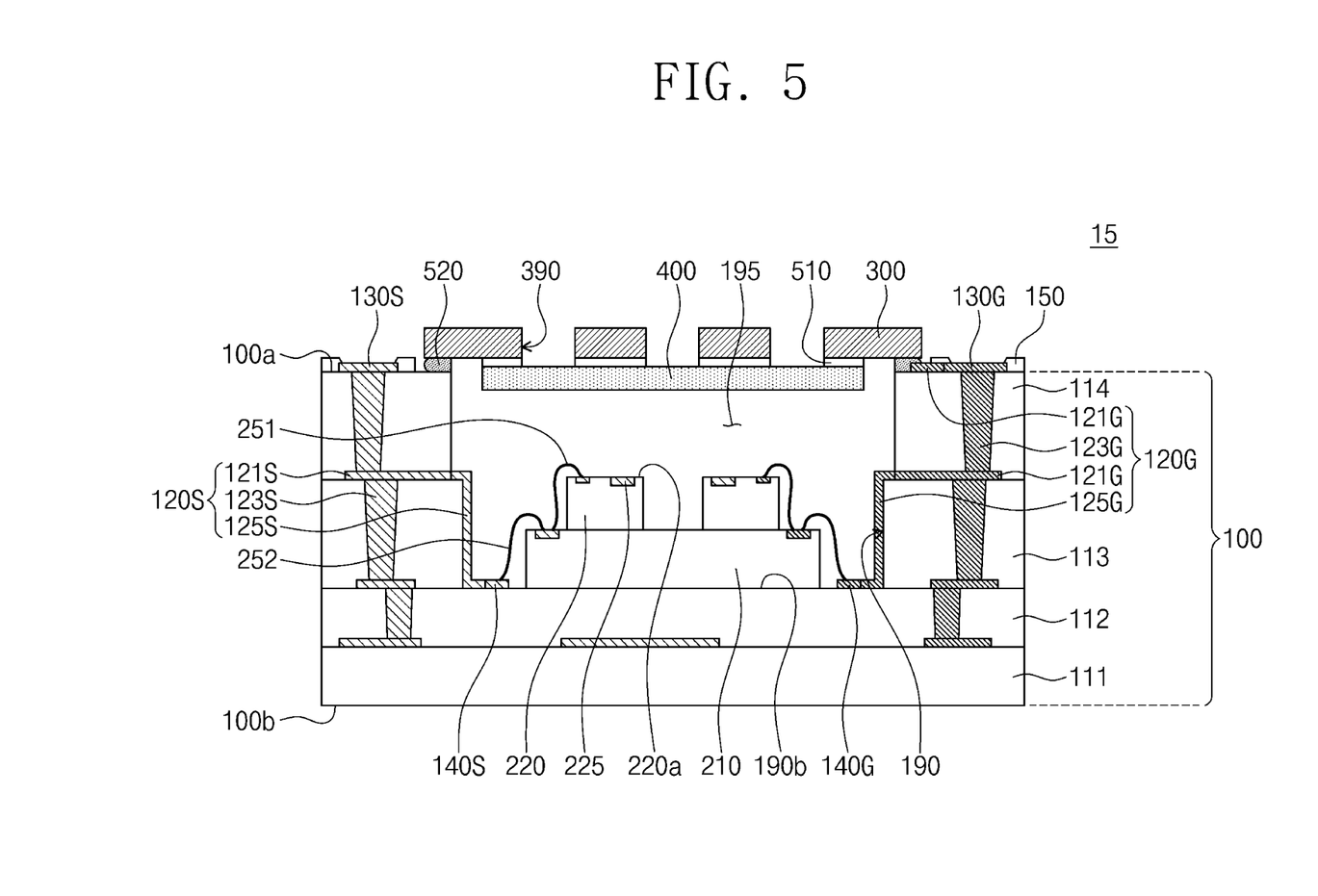
FIG. 5 is a cross-sectional view illustrating a gas sensor package according to some exemplary embodiments of the inventive concepts.

FIG. 5 is a cross-sectional view illustrating a gas sensor package according to some embodiments of the inventive concepts. Hereinafter, the descriptions to the same elements and technical features as in the above embodiments will be omitted or mentioned briefly for the purpose of ease and convenience in explanation.

Referring to FIG. 5, a gas sensor package 15 may include a package substrate 100, a control device 210, a sensing device 220, a fixing plate 300, and a protective film 400. The control device 210, the sensing device 220, the fixing plate 300 and the protective film 400 may be substantially the same as described above with reference to FIGS. 1A and 1B, 1C, or 2A and 2B. First and second lower base layers 111 and 112 and first and second upper base layers 113 and 114 of the package substrate 100 may be substantially the same as described with reference to FIG. 4. However, a signal structure 120S may further include a signal redistribution pattern 125S in addition to the signal pattern 121S and the signal via 123S. The signal redistribution pattern 125S may be electrically connected to the signal pattern 121S and the signal via 123S. The signal redistribution pattern 125S may extend along the top surface of the first upper base layer 113, a portion of a sidewall of the hole 190 (e.g., a sidewall of the first upper base layer 113), and the bottom surface 190b of the hole 190. The signal redistribution pattern 125S may be connected to the signal bonding pad 140S. In this exemplary embodiment, the signal bonding pad 140S may be disposed on the bottom surface 190b of the hole 190. A ground structure 120G may further include a ground redistribution pattern 125G in addition to the ground pattern 121G and the ground via 123G. The ground redistribution pattern 125G may be provided on the top surface of the first upper base layer 113 so as to be electrically connected to the ground pattern 121G. The ground redistribution pattern 125G may extend along a portion of the sidewall of the hole 190 (e.g., a sidewall of the first upper base layer 113) and the bottom surface 190b of the hole 190. The ground redistribution pattern 125G may be connected to the ground bonding pad 140G. In this exemplary embodiment, the ground bonding pad 140G may be disposed on the bottom surface 190b of the hole 190. The ground redistribution pattern 125G may be spaced apart from the signal redistribution pattern 125S. The ground redistribution pattern 125G may be electrically insulated from the signal redistribution pattern 125S. The redistribution patterns 125S and 125G may include a metal such as copper or aluminum.

Unlike FIG. 5, the signal and ground redistribution patterns 125S and 125G may be disposed on a top surface of the second upper base layer 114 and may extend along sidewalls of the first and second upper base layers 113 and 114 and the bottom surface 190b of the hole 190. For example, the signal redistribution pattern 125S may be connected to the signal pad 130S and the signal bonding pad 140S. The ground redistribution pattern 125G may be connected to the ground pad 130G and the ground bonding pad 140G.

A ground pattern 121G on the second upper base layer 114 may be connected directly to the ground pad 130G. In certain embodiments, the ground via 123G may be provided between the ground pattern 121G on the second upper base layer 114 and the ground pattern 121G on the first upper base layer 113, and the ground pattern 121G on the second upper base layer 114 may be electrically connected to the ground pad 130G through the ground via 123G, as illustrated in FIG. 4.

Figure 6:
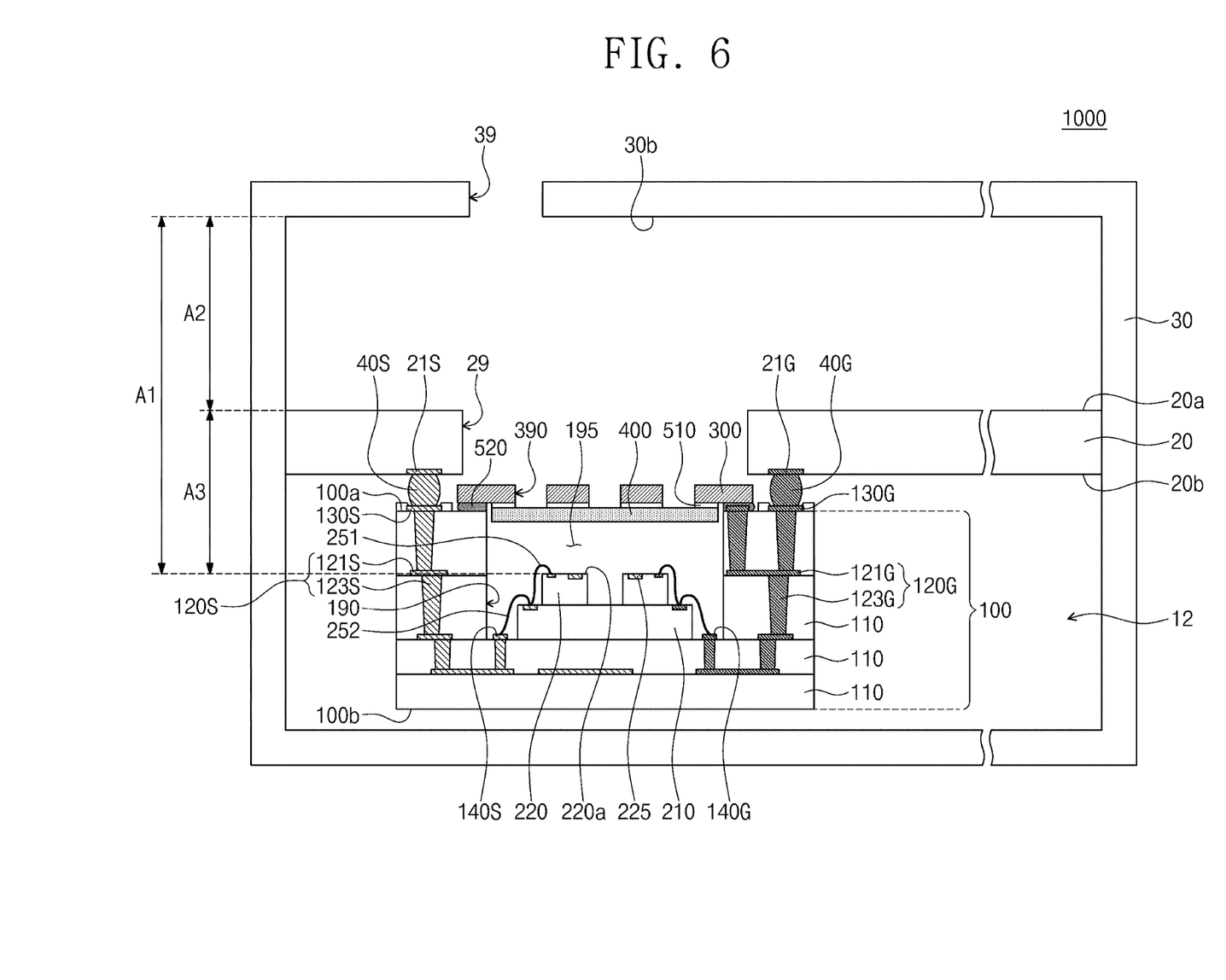
FIG. 6 is a cross-sectional view illustrating a sensing apparatus according to some exemplary embodiments of the inventive concepts.

FIG. 6 is a cross-sectional view illustrating a sensing apparatus according to some exemplary embodiments of the inventive concepts. Hereinafter, the descriptions to the same elements and technical features as in the above embodiments will be omitted or mentioned briefly for the purpose of ease and convenience in explanation.

Referring to FIG. 6, a sensing apparatus 1000 may include a module board 20, a gas sensor package 12, and a frame 30. The sensing apparatus 1000 may sense or measure a gas. In some embodiments, the sensing apparatus 1000 may be an electronic apparatus such as a portable phone. For example, the electronic apparatus may perform a gas sensing function.

The frame 30 may be a case of the sensing apparatus 1000. The module board 20 may be provided in the frame 30. The module board 20 may include, but not limited to, a printed circuit board. The module board 20 may have one surface 20b (e.g., bottom surface) and another surface 20a (e.g., top surface) opposite to the one surface 20b. The surface 20b may face the package substrate 100 and the surface 20a may face away from the substrate package. The module board 20 may have an air hole 29 penetrating the module board 20. The air hole 29 may penetrate the one surface 20b and the other surface 20a of the module board 20. For example, the air hole 29 may extend between the one surface 20b and the other surface 20a of the module board 20. Conductive pads 21S and 21G may be disposed on the one surface 20b of the module board 20. The conductive pads 21S and 21G may include a signal conductive pad 21S and a ground conductive pad 21G.

The gas sensor package 12 may be mounted on the module board 20. The gas sensor package 12 may overlap the air hole 29 when viewed in a plan view. The gas sensor package 12 may be the gas sensor package 12 described with reference to FIGS. 2A and 2B. Alternatively, one of the gas sensor packages 10, 11, 13, 14 and 15 of FIGS. 1A to 1C and 3 to 5 may be mounted on the module board 20.

In some embodiments, the gas sensor package 12 may be mounted on the one surface 20b of the module board 20. The gas sensor package 12 may be disposed on the module board 20 in such a way that the first surface 100a of the package substrate 100 faces the module board 20. Solders 40S and 40G may be provided on the first surface 100a of the package substrate 100. The solders 40S and 40G may be disposed between the package substrate 100 and the module board 20 to electrically connect the gas sensor package 12 to the module board 20. The solders 40S and 40G may include a signal solder 40S and a ground solder 40G. The signal solder 40S may be disposed between the signal pad 130S and the signal conductive pad 21S. Electrical signals outputted from the sensing devices 220 and the control device 210 may be transferred to an external apparatus (not shown) through the signal structure 120S, the signal solder 40S, and the module board 20. The electrical signals may include signals of gas sensing results measured from the sensing devices 220. The ground solder 40G may be disposed between the ground pad 130G and the ground conductive pad 21G. The ground solder 40G may be connected to the ground pad 130G and the ground conductive pad 21G. The sensing devices 220, the control device 210 and the fixing plate 300 may receive a ground voltage through the ground solder 40G. The signal and ground solders 40S and 40G may include a metal, e.g., tin (Sn), lead (Pb), indium (In), or any alloy thereof.

The top surfaces 220a of the sensing devices 220 may face an inner surface 30b of the frame 30. As described above, the top surfaces 220a of the sensing devices 220 may function as the sensing surfaces. An external gas may flow into the sensing apparatus 1000 through an external vent hole 39 of the frame 30. As the amount of the gas transferred to the sensing devices 220 increases, the sensing accuracy of the sensing devices 220 may be improved. In the event that the gas sensor package 12 is mounted on the other surface 20a of the module board 20, a distance between the frame 30 and the sensing devices 220 may be less than a distance A2 between the frame 30 and the other surface 20a of the module board 20. In some embodiments, the gas sensor package 12 may be mounted on the one surface 20b of the module board 20, as described above. Thus, a distance A1 between the frame 30 and the sensing devices 220 in a direction perpendicular to the first surface 100a of the package substrate 100 may be greater than the distance A2 between the frame 30 and the other surface 20a of the module board 20 in the direction perpendicular to the first surface 100a of the package substrate 100. According to the inventive concepts, since the sensing devices 220 are disposed in the hole 190 of the package substrate 100, the sensing devices 220 may be further away from the frame 30. According to some embodiments, the distance A1 between the frame 30 and the sensing devices 220 in the direction perpendicular to the first surface 100a of the package substrate 100 may be substantially equal to a sum of the distance A2 between the frame 30 and the other surface 20a of the module board 20 and a distance A3 between the other surface 20a of the module board 20 and the top surfaces 220a of the sensing devices 220 in the direction perpendicular to the first surface 100a of the package substrate 100. The gas provided through the external vent hole 39 may be transferred to the sensing devices 220 through the air hole 29, the vent hole 390, the protective film 400, and the hole 190. Thus, the amount of the gas transferred to the sensing devices 220 may be increased to improve the sensing accuracy of the sensing devices 220.

At least one semiconductor device (not shown) may further be mounted on the one surface 20b or the other surface 20a of the module board 20. The semiconductor device may include at least one of memory devices and logic devices.

According to some embodiments of the inventive concepts, the sensing devices may be disposed in the hole of the package substrate, and thus a greater amount of the gas may be transferred to the sensing devices. As a result, the sensing accuracy of the sensing devices may be improved.

According to some embodiments of the inventive concepts, the protective film may prevent the impurities from flowing into the hole of the package substrate. Thus, it is possible to reduce or prevent sensing noise and damage of the sensing devices, which may be caused by the impurities. The protective film may be firmly fixed to the fixing plate.

While the inventive concepts have been described with reference to example embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. A gas sensor package comprising:
    a package substrate having a hole, the hole extending from a first surface of the package substrate toward a second surface of the package substrate that is opposite to the first surface of the package substrate, and the hole forming an opening in the first surface of the package substrate and having a bottom closed surface at a location between the first surface of the package substrate and the second surface of the package substrate;
    a first gas sensor disposed in the hole of the package substrate;
    a fixing plate disposed on the first surface of the package substrate, the fixing plate having a vent hole extending between a top surface and a bottom surface of the fixing plate, the bottom surface of the fixing plate facing toward the package substrate and the top surface of the fixing plate facing away from the package substrate, and the fixing plate overlapping the hole of the package substrate when viewed in a plan view;
    a protective film attached to the fixing plates; and
    a ground pad disposed on the first surface of the package substrate,
    wherein the protective film overlaps the vent hole when viewed in a plan view
    wherein the bottom surface of the fixing plate faces a top surface of the first gas sensor and is spaced from the top surface of the first gas sensor, and
    wherein the first surface of the package substrate is disposed at a higher level than the top surface of the first gas sensor.

2. The gas sensor package of claim 1,
    wherein the vent hole of the fixing plate overlaps the hole of the package substrate when viewed in a plan view.

3. The gas sensor package of claim 1,
    wherein the package substrate comprises:
    a signal structure electrically connected to the first gas sensor, wherein the signal structure includes a first conductive pattern and a first conductive via which are electrically connected to each other; and
    a ground structure electrically connected to the fixing plate, wherein the ground structure includes a second conductive pattern and a second conductive via which are electrically connected to each other, wherein the ground structure is insulated from the signal structure, wherein the first conductive pattern has a width smaller than that of the first conductive via, and wherein the second conductive pattern has a width smaller than that of the second conductive via.

4. The gas sensor package of claim 3, further comprising:
a conductive adhesive portion disposed between the first surface of the package substrate and the fixing plate, wherein a portion of the ground structure is exposed on the first surface of the package substrate, and wherein the conductive adhesive portion extends between the exposed portion of the ground structure and the fixing plate.

5. The gas sensor package of claim 3,
wherein the ground pad is electrically connected to the fixing plate through the ground structure.

6. The gas sensor package of claim 3,
wherein the first gas sensor is electrically connected to the ground structure.

7. The gas sensor package of claim 1,
wherein the protective film includes a hydrophobic polymer, and wherein the protective film allows a gas to pass through.

8. The gas sensor package of claim 1, further comprising:
a controller provided in the hole of the package substrate and on the bottom closed surface of the hole of the package substrate, wherein the first gas sensor is stacked on a top surface of the controller.

9. The gas sensor package of claim 8, further comprising:
a first bonding wire connecting the controller to the first gas sensor.

10. The gas sensor package of claim 8, further comprising:
a second gas sensor is stacked on the top surface of the controller, wherein the first gas sensor and the second gas sensor are spaced apart from each other on the top surface of the controller.

11. The gas sensor package of claim 1,
wherein the package substrate comprises a first base layer and a second base layer, which are sequentially stacked, wherein the second base layer exposes a portion of a top surface of the first base layer, wherein a bonding pad is disposed on the exposed portion of the top surface of the first base layer, and wherein the first gas sensor is electrically connected to the bonding pad.

12. A sensing apparatus comprising:
a module board having a first hole extending between a top surface and a bottom surface of the module board; and a gas sensor package mounted on the module board and overlapping the first hole when viewed in a plan view, wherein the gas sensor package comprises:

a package substrate having a second hole, the second hole having an end that is opened at a first surface of the package substrate;

a gas sensor disposed in the second hole of the package substrate;

a fixing plate disposed on the first surface of the package substrate, the fixing plate having a vent hole extending between a top surface of the fixing plate and a bottom surface of the fixing plate, the bottom surface of the fixing plate facing toward the package substrate and the top surface of the fixing plate facing away from the package substrate, the fixing plate overlapping the second hole of the package substrate when viewed in a plan view; and a protective film attached to the fixing plate, wherein the first surface of the package substrate faces the module board, and wherein the bottom surface of the fixing plate faces a top surface of the gas sensor and spaced from the top surface of the gas sensor.

13. The sensing apparatus of claim 12,
wherein the vent hole overlaps the protective film when viewed in a plan view, and wherein the first surface of the package substrate is disposed at a higher level than the top surface of the gas sensor.

14. The sensing apparatus of claim 12, further comprising:
a ground solder provided between the first surface of the package substrate and the module board, wherein the fixing plate is electrically connected to the ground solder through the package substrate.

15. The sensing apparatus of claim 14, further comprising:
a signal solder provided between the first surface of the package substrate and the module board, wherein the signal solder is insulated from the fixing plate.

16. The sensing apparatus of claim 14,
wherein the gas sensor is electrically connected to the ground solder.

17. The sensing apparatus of claim 12, wherein the vent hole overlaps the second hole of the package substrate when viewed in a plan view.

18. The sensing apparatus of claim 12, wherein the vent hole overlaps the first hole of the module board when viewed in a plan view.

19. The sensing apparatus of claim 12,
wherein a width of the fixing plate is greater than a width of the second hole of the package substrate.

20. The sensing apparatus of claim 12, wherein the protective film includes a waterproof film, and wherein the waterproof film has pores each having a diameter ranging from 0.1 μm to 10 μm.

* * * * *